United States Patent [19]

Akui et al.

[11] Patent Number: 4,715,360

[45] Date of Patent: Dec. 29, 1987

[54] ENDOSCOPE FORCEPS STOPCOCK

[75] Inventors: Nobuaki Akui; Yasuhiro Ueda; Akira Suzuki, all of Tokyo, Japan

[73] Assignee: Olympus Optical Co., Ltd., Japan

[21] Appl. No.: 1,157

[22] Filed: Jan. 7, 1987

Related U.S. Application Data

[62] Division of Ser. No. 773,122, Sep. 6, 1985, Pat. No. 4,653,477.

[30] Foreign Application Priority Data

| Sep. 13, 1984 [JP] | Japan | 59-139279 |
| Oct. 5, 1984 [JP] | Japan | 59-209455 |
| May 22, 1985 [JP] | Japan | 60-109573 |

[51] Int. Cl.$^4$ ............................................. A61B 1/00
[52] U.S. Cl. .................................... 128/4; 128/912; 604/256
[58] Field of Search .................. 128/4, 6, 912, 348; 604/256, 280

[56] References Cited

U.S. PATENT DOCUMENTS

| 4,000,739 | 1/1977 | Stevens | 604/280 |
| 4,177,814 | 12/1979 | Knepshied et al. | 128/348 |
| 4,240,411 | 12/1980 | Hosono | 128/4 |
| 4,416,273 | 11/1983 | Grimes | 128/912 X |
| 4,436,519 | 3/1984 | O'Neill | 604/256 X |
| 4,653,477 | 3/1987 | Akui et al. | 128/4 |

FOREIGN PATENT DOCUMENTS 2623511 2/1977 Fed. Rep. of Germany .

*Primary Examiner*—William H. Grieb

[57] ABSTRACT

An endoscope forceps stopcock has a cylindrical body. The body has a lower engagement section detachably fitted to an insertion mouthpiece of an endoscope, and an upper engagement section to which a cap is detachably fitted. The body and cap are connected to each other by a coupling member. A valve section is formed in the body between the engagement sections to close an insertion channel and provided with a pushing section and an insertion section allowing for the insertion of medical operation instruments. The pushing section presses the cap in accordance with the extent of the deformation of the valve section when the pressure in the insertion channel is increased, thereby holding the cap in cooperation with the upper engagement section.

12 Claims, 14 Drawing Figures

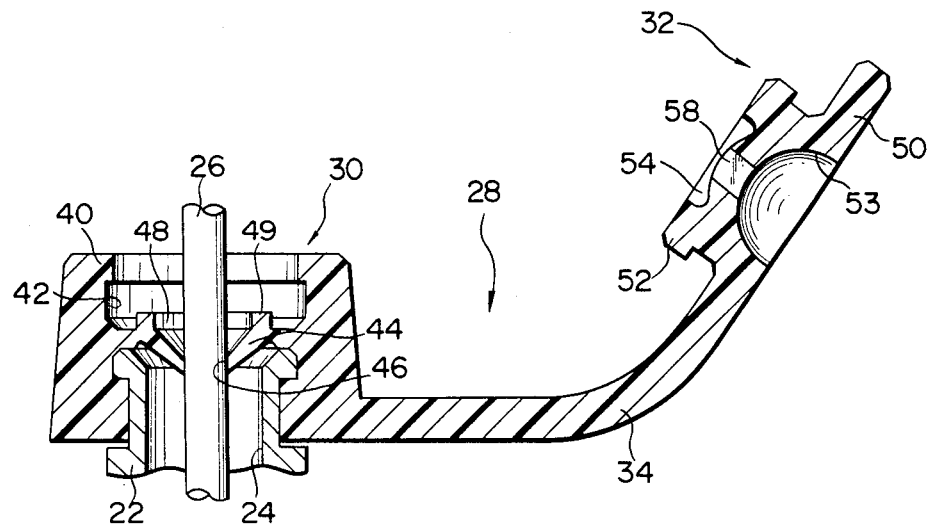
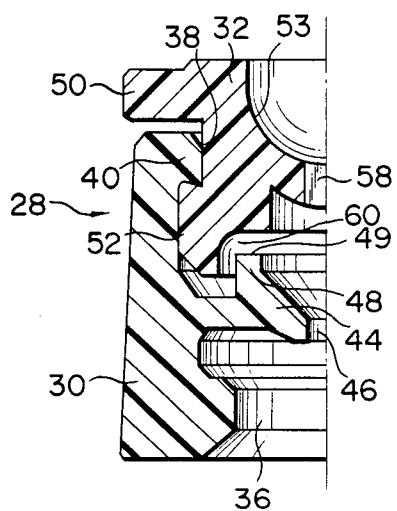
FIG. 6
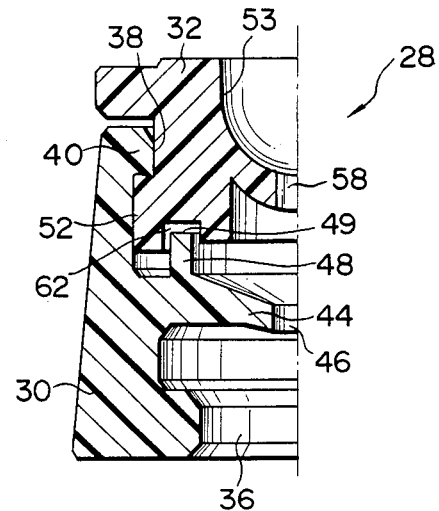
FIG. 7

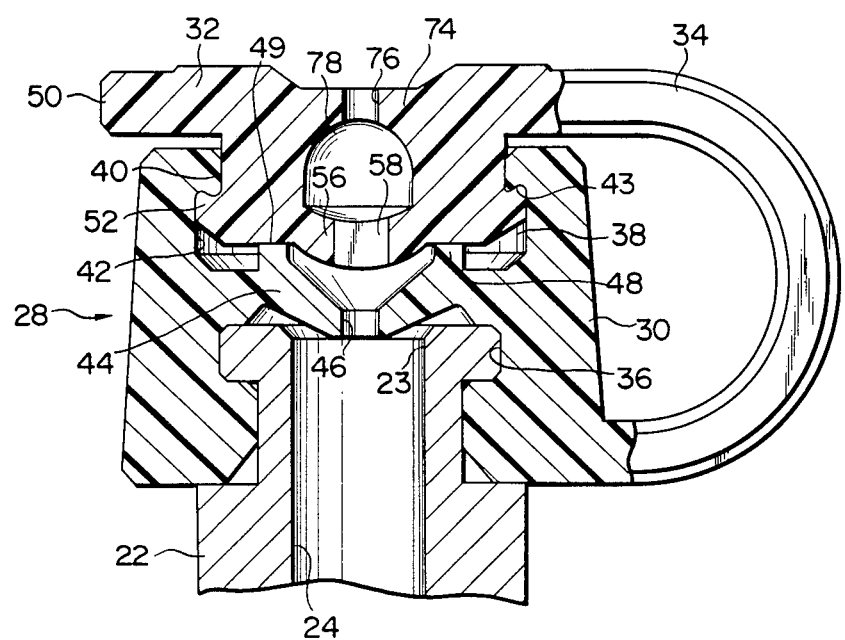
F I G. 14

ENDOSCOPE FORCEPS STOPCOCK

This is a division of application Ser. No. 773,122, filed Sept. 6, 1985, now U.S. Pat. No. 4,653,477, granted Mar. 31, 1987.

BACKGROUND OF THE INVENTION

This invention relates to a forceps stopcock to close the port of an endoscope channel allowing for the insertion of medical operation instruments.

When a medical examination or operation is carried out by means of an endoscope, the endoscope is generally inserted into the patient's coeliac cavity. In this case, various operations are taken through the endoscope. For instance, a medical solution is injected into the patient's coeliac cavity or his affected portion is excised or sampled. To this end, therefore, the endoscope is provided with an insertion channel allowing for the insertion of instruments used to carry out the above-mentioned medical operations. During the application of the endoscope, however, it sometimes happens that air or filth held in the coeliac cavity leaks to the outside through the insertion channel. In such a case, the leakage of air or filth from the coeliac cavity has hitherto been prevented by fitting a forceps stopcock to the insertion channel port. This stopcock is prepared from elastic material such as rubber and provided with a slit allowing for the insertion of a medical operation instrument. The slit is usually closed in an airtight fashion, and is opened when forcefully pushed by a medical operation instrument, thereby enabling the instrument to be inserted into the channel.

When, however, a medical operation instrument is inserted into the slit, it sometimes happens that gaps appear between the slit and the medical operation instrument, resulting in the leakage of air or filth conducted from the patient's coeliac cavity.

To avoid the above-mentioned drawbacks, therefore, a forceps stopcock has been proposed which is constructed by superposing an elastic stopcock having a slit and an elastic stopcock having a through hole with a smaller diameter than that of a medical operation instrument on each other. This composite plug is constructed by tightly holding the pair of superposed plugs by means of a tightening ring, and is securely held in the insertion channel port by means of a fixed ring. However, such a composite forceps stopcock has the drawback that difficulties are presented in fitting the stopcock into the endoscope, taking it out of the insertion channel port and cleaning the whole stopcock assembly.

SUMMARY OF THE INVENTION

This invention has been accomplished in view of the above-mentioned circumstances and is intended to provide an endoscope forceps stopcock which reliably closes the insertion channel port, prevents the leakage of, for example, air or filth from the patient's coeliac cavity and facilitates the detachable insertion of a forceps stopcock into the insertion channel port and also the cleaning of the forceps stopcock.

To attain the above-mentioned object, this invention provides an endoscope forceps stopcock which comprises:

a substantially cylindrical body prepared from elastic material and fitted to the insertion mouthpiece of the endoscope, said cylindrical body including an engagement section formed at one end opening thereof to be detachably fitted to the insertion mouthpiece, another engagement section provided at the other end opening thereof, and a valve section which is formed in the inner hole of the body between the both engagement sections so as to close the insertion channel port, is provided with an insertion section allowing for the insertion of the medical operation instruments and further is made elastically deformable in the axial direction of the insertion channel to an extent corresponding to the magnitude of the internal pressure in the insertion channel; and a cap member detachably fitted to the other engagement section of the cylindrical body, said valve section being provided with a pressing section which presses the cap member in accordance with the deformation of the valve section caused by an increase in the internal pressure in the insertion channel so as to hold the cap member in cooperation with the other end engagement section.

BRIEF DESCRIPTION OF THE DRAWINGS

FIGS. 1 to 5 illustrate a forceps stopcock according to a first embodiment of this invention in which: FIG. 1 is a side view of an endoscope fitted with the stopcock; FIG. 2 is a sectional view of the stopcock engaged with the insertion channel port; FIGS. 3 and 4 are respectively fractionally exploded side and plan views of the developed stopcock; and FIG. 5 is a sectional view of the stopcock whose cap member is opened;

FIGS. 6 and 7 are fractional sectional views of forceps stopcocks according to first and second modifications of the invention, respectively;

FIGS. 8 and 9 illustrate a forceps stopcock according to a second embodiment of the invention; in which FIG. 8 is a sectional view showing the stopcock which is not engaged with the insertion channel port, and FIG. 9 is a sectional view of the stopcock engaged with the insertion channel port;

FIGS. 11 and 12 show a forceps stopcock according to a fourth embodiment of the invention; in which FIG. 11 is a sectional view of the stopcock which is engaged with the insertion channel port, and FIG. 12 is an enlarged sectional view showing part of the stopcock;

FIG. 14 is a sectional view of a forcpes stopcock according to a sixth embodiment of the invention.

DETAILED DESCRIPTION OF THE PREFERRED EMBODIMENT

Figure 1:
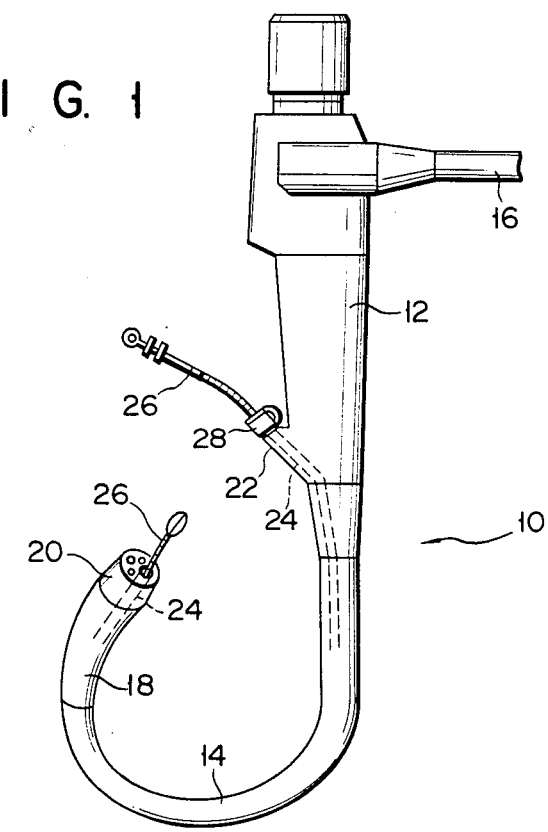

Description may now be made with reference to the accompanying drawings of the forceps stopcocks according to the various embodiments of this invention. As shown in FIG. 1, an endoscope 10 comprises an operation section 12, an insertion section 14 extending out of the operation section 12, and a universal cord 16 extending from the operation section 12. The extended end of the universal cord 16 is connected to a light source (not shown). The distal end of the insertion section 14 is fitted with a distal end structure 20 with a flexible section 18 set adjacent thereto. The operation section 12 is provided with an insertion mouthpiece 22 having an insertion port 23. The mouthpiece 22 communicates with an insertion channel 24 which extends through the insertion section 14 and flexible section 18 and is open to the distal end structure 20. A medical operation instrument, for example, biopsic forceps 26 is taken into the insertion channel 24 through the insertion port 23. The mouthpiece 22 is fitted with a forceps stopcock 28 embodying this invention to close the insertion port 23.

Figure 2:
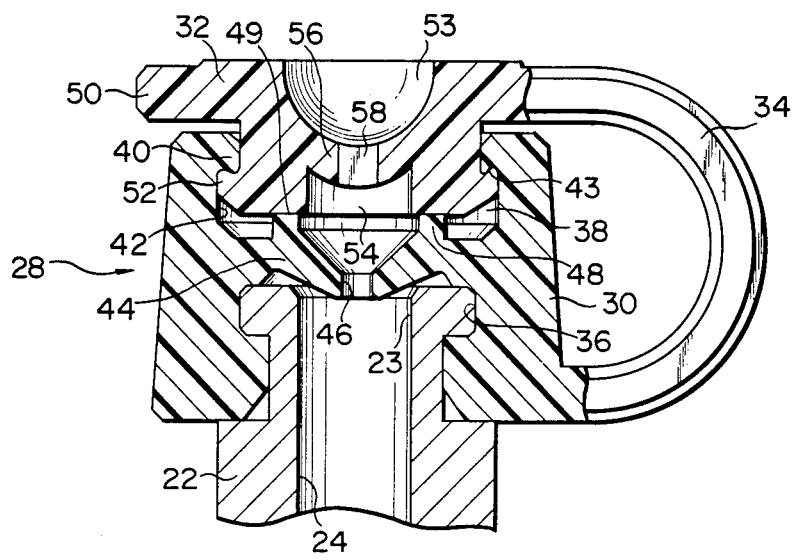
Figure 3:
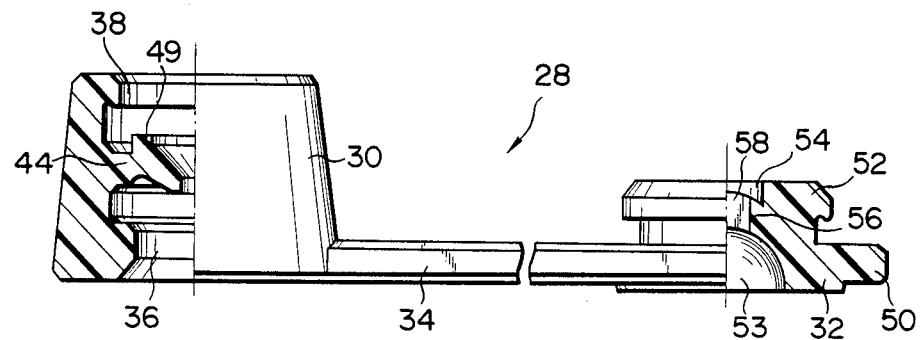
Figure 4:
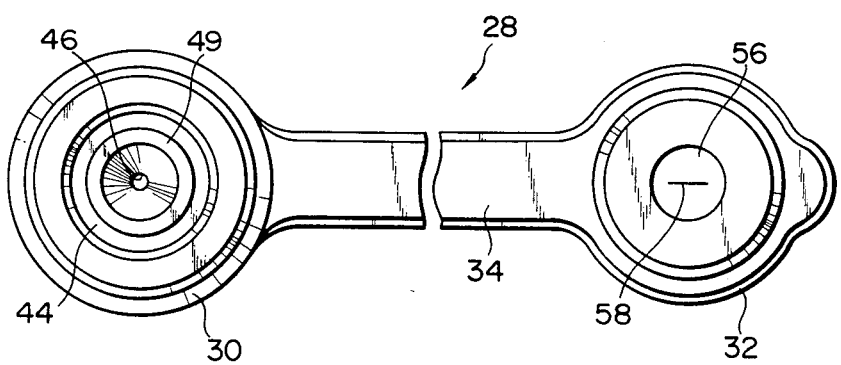

As seen from FIGS. 2 to 4, the forceps stopcock 28 includes a round cylindrical body 30, a cap 32 and a coupling member 34 for effecting connection between the cylindrical body 30 and cap 32. The cylindrical body 30, cap 32 and coupling member 34 are integrally fabricated from an elastic material such as silicone rubber, fluorine rubber or nitrile butyl rubber.

Formed in the lower opening of the cylindrical body 30 is a lower engagement section 36 which is detachably meshed with the insertion mouthpiece 22. Provided in the upper opening of the cylindrical body 30 is an upper engagement section member 38 with which the cap 32 is detachably meshed. The upper engagement section 38 includes an annular flange 40 projecting radially inward from the upper end inner periphery of the cylindrical body 30 and an annular groove 42 formed below the annular flange 40. The flange 40 and annular groove 42 are made coaxially with the insertion port 23. An annular shoulder section 43 is formed between the annular flange 40 and annular groove 42.

Formed between the upper engagement section 38 and lower engagement section 36 of the cylindrical body 30 is a relatively thin valve section 44 to close the insertion port 23. Provided at the center of the valve section 44 is an insertion hole 46 as an insertion section allowing for the insertion of the forceps 26. This insertion hole 46 has a smaller diameter than the forceps and is coaxially formed with the insertion port 23. The valve section 44 includes an annular pushing member 48 projecting upward. The upper surface of the pushing member 48 acts as a pressing plane 49. The pushing member 48 is formed coaxially with the insertion port 23 and is set substantially opposite to the shoulder section 43 of the upper engagement section 38. The thin-walled valve section 44 is elastically deformed in the axial direction of the insertion channel 24 to an extent corresponding to the magnitude of the internal pressure in the insertion channel. In other words, when the internal pressure in the insertion channel 24 rises, the valve section 44 is elastically deformed upward.

The cap 32 is made substantially in the form of a round column. The outer diameter of the cap 32 is made substantially equal to the inner diameter of the annular flange 40 of the upper engagement section 38. The upper periphery of the cap 32 is provided with a flange 50 which projects radially outward. The lower periphery of the cap 32 is provided with a flange 52 which also projects radially outward. The outer diameter of the flange 52 is made equal to the diameter of the annular groove 42 of the upper engagement section 38. A semispherical depression 53 is formed at the center of the flange 50. A depression 54 whose bottom is spherically projected is formed at the center of the flange 52. A thin walled section 56 is formed between the depressions 53, 54. A straight line slit 58 is formed at the center of the thin-walled section 56 to allow for the insertion of the forceps 26. This slit 58 is made longer than the diameter of the forceps 26. The slit may assume the form of a cross or the letter Y in place of a straight line. The slit is generally closed in an air-tight fashion.

While the cap 32 is meshed with the upper engagement section 38 of the cylindrical body 30, the flange 52 is meshed with the annular groove 42 of the upper engagement section 38, and the upper edge of the flange 52 is meshed with the shoulder section 43. Thus the cap 32 is detachably engaged with the cylindrical body 30. Under this condition, the underside of the flange 52 is pressed against the pressing plane 49 of the pushing member 48. When the internal pressure in the insertion channel 24 rises, the flange 52 of the cap 32 is held between the shoulder 43 and the pressing plane 49, thus causing the cap 32 to be securely engaged with the cylindrical body 30.

The coupling member 34 has a substantially rectangular cross section, and is connected at one end to the lower outer periphery of the body 30 and at the other end to the flange 50 of the cap 32.

When a medical operation is performed by using an instrument such as the biopsic forceps 26, first the insertion section 14 of the endoscope 10 is inserted into the patent's coeliac cavity. A this time, the forceps stopcock 28 is fitted to the mouthpiece 22 and the cap 32 is fitted to the cylinrical body 30. Under this condition, the slit 58 of the cap 32 is closed in an air-tight fashion, causing the insertion port 23 to be closed in an air-tight fashion by the forceps stopcock 28. When the forceps 26 are inserted into the insertion channel 24 through the stopcock 28, the distal end of the forceps 26 is brought to the slit 58 by being guided by the depression 53 of the cap 32. The distal end of the forceps 26 is forced through the slit 58 and brought into the insertion channel 24 through the insertion hole 46 of the cylindrical body 30. Later as shown in FIG. 1, the forceps 26 are pushed inward until the distal end of the forceps 26 protrudes from the distal end structure 20 of the endoscope. Under this condition, the prescribed medical operation is carried out. While the forceps 26 are inserted into the insertion channel 24, the slit 58 is tightly attached to the forceps 26 due to its elastic deformation, and the insertion hole 46 has a smaller diameter than the forceps 26 and also tightly contacts the forceps 26. While, therefore, the forceps 26 are inserted, the insertion channel 24 can be kept in an airtight condition. The forceps 26 can be easily inserted into the endoscope channel 24, if the cap 32 is removed from the cylindrical body 30, as shown in FIG. 5.

With the forceps stopcock 28 constructed as described above, the cylindrical body 30 alone is fitted into the insertion mouthpiece 22 of the endoscope 10 and the cap 32 is meshed with the cylindrical body 30, thereby facilitating the detachable fitting of the forceps stopcock 28 to the insertion mouthpiece 22 and the washing of the forceps stopcock 28. Since the slit 58 is generally air-tightly closed while the cap 32 is engaged with the cylindrical body 30, the insertion port 23 of the mouthpiece 22 can be closed in an air-tight fashion. When the endoscope stops suction, or the internal pressure in the insertion channel 24 rises by the pressure prevailing, for example, in the patient's stomach, the cap 32 is so pressed toward the direction in which it otherwise would be taken off the cylindrical body 30. When, however, with the foregoing embodiment, the internal pressure in the insertion channel 24 rises, the valve section 44 is elastically deformed upward, namely, toward the cap 32. As a result, the pressing plane 49 of the pushing member 48 moves the cap 32 upward, causing the flange 52 of the cap 32 to be clamped between the shoulder section 43 and the pressing plane 49. Even when, therefore, the internal pressure in the insertion channel 24 rises, the cap 32 remains engaged with the cylindrical body 30. Consequently, the forceps stopcock 28 reliably prevents the leakage of air or filth from the insertion channel 24. Ordinarily, the flange 52 of the cap 32 is not held between the pushing member 48 and shoulder section 43, thereby facilitating the removal of the cap 32 from the cylindrical body 30.

As shown in FIG. 5, the forceps 26 can be inserted into the insertion channel 24 with the cap 32 taken off. In this case, the forceps can be taken into and out of the insertion channel with a small force without the necessity of forcing open the slit 58 of the cap 32. Consequently, the forceps can be easily inserted and drawn out, thus allowing for the application of an elastic medical operation member such as a tube. The cylindrical body 30 and cap 32 are connected together. Therefore, even when the cap 32 is taken out of the cylindrical body 30, the cap 32 need not be held by the hand, nor is it likely to be lost. Moreover, the cylindrical body 30, cap 32 and connecting section 34 are integrally prepared from elastic material, ensuring the inexpensive manufacture of the forceps stopcock.

In the aforementioned embodiment, the connecting section 34 need not be provided. Still, substantially the same effect can be realized as in the foregoing embodiment. The cap 32 need not be provided with the slit 58 allowing for the insertion of the forceps 26. In such case, the cap 32 is always taken off the cylindrical body when the forceps 26 is inserted into the insertion channel. Further, in this case, the insertion hole 46 may be replaced by a slit to effect the insertion of the forceps 26.

FIGS. 6 and 7 respectively show the first and second modifications of the subject endoscope forceps stopcock. The parts of FIGS. 6 and 7 which are the same as those of the preceding embodiment are denoted by the same numerals, description thereof being omitted.

In the first modification of FIG. 6, an escape depression 60 is formed in the flange 52 of the cap 32 to prevent the pushing member 48 of the valve section 44 from touching the flange 52. When, therefore, a low pressure prevails in the insertion channel, the pressing plane 49 of the pushing member 48 does not conflict with the cap 32, thereby facilitating its detachable fitting. When the internal pressure in the insertion channel rises, the valve section 44 is deformed, obviously causing the flange 52 of the cap 32 to be pressed by the pressing plane 49 due to the elastic deformation of the valve section 44.

In the second modification of FIG. 7, an annular escape groove 62 is provided in the flange 52 so as to face the pushing member 48 to replace the above mentioned escape depression 60. This second embodiment attains the same effect as the above mentioned first modification.

Figure 8:
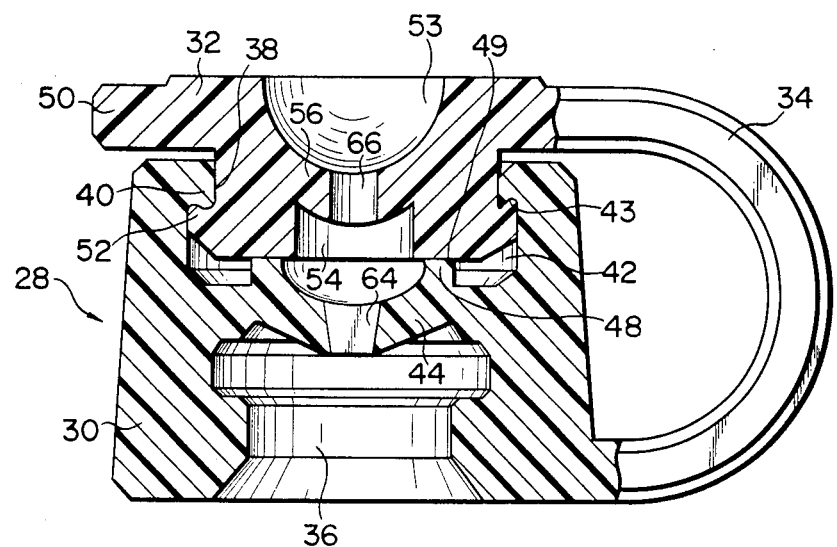
Figure 9:
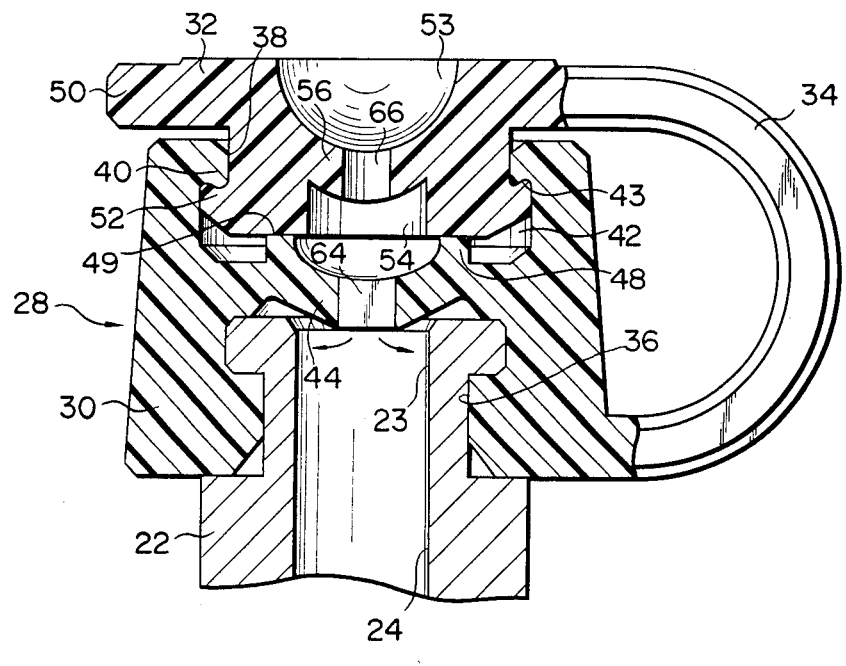

FIGS. 8 and 9 jointly show the forceps stopcock according to a second embodiment of this invention. A slit 64 as an insertion section is formed in the valve section 44 of the cylindrical body 30 to allow for the insertion of the forceps 26. The thin-walled section 56 of the cap 32 is provided with an insertion hole 66 to allow for the insertion of the forceps 26. As shown in FIG. 8, the slit 64 is so shaped that the upper end portion is made wider and the lower end portion is made narrower. The second embodiment indicates the undermentioned effect in addition to that of the first embodiment. With the second embodiment, the forceps insertion section of the cylindrical body 30 is made in the form of a slit 64. Even when, therefore, the cap 32 is taken off, the insertion port 23 of the insertion mouthpiece 22 can be closed in an airtight fashion. When the cylindrical body 30 is engaged with the mouthpiece 22, the valve section 44 is radially drawn outward as shown by the arrows of FIG. 9. Consequently the slit 64 tends to be opened. However, as mentioned above, the slit 64 is made narrower toward the lower end. Even when, therefore, the valve section 44 is elastically pulled, the lower end of the slit 64 is made substantially as wide as the upper end. Even when, therefore, the cylindrical body 30 is engaged with the mouthpiece 22, the slit 64 is kept in an airtight condition, thereby preventing the leakage of air or filth from the insertion channel 24.

Figure 10:
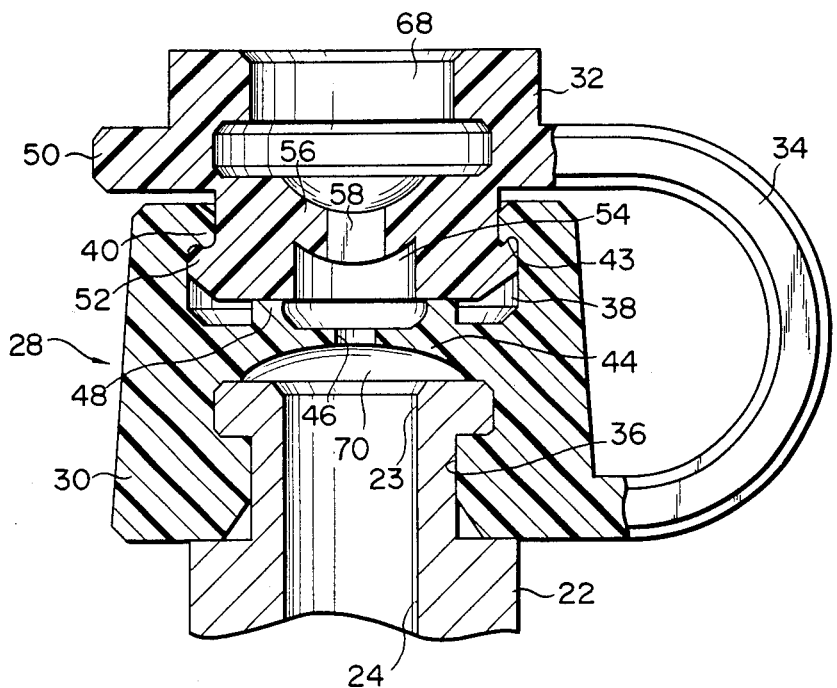
FIG. 10 is a sectional view of a forceps stopcock according to a third embodiment of the invention which is engaged with the insertion channel port.

FIG. 10 shows a forceps stopcock according to a third embodiment of this invention. In this third embodiment, a cap side engagement section 68 capable of being engaged with the insertion mouthpiece 22 is formed at that end of the cap 32 which faces the flange 50. An arcuate depression 70 is formed on the underside of the valve section 44. With the third embodiment of FIG. 10, the cap 32 can be engaged with the mouthpiece 22 in place of the cylindrical body 30, and the cylindrical body can be applied as a cap. In this case the depression 70 of the valve section 44 guides the forceps into the insertion hole 46.

Figure 11:
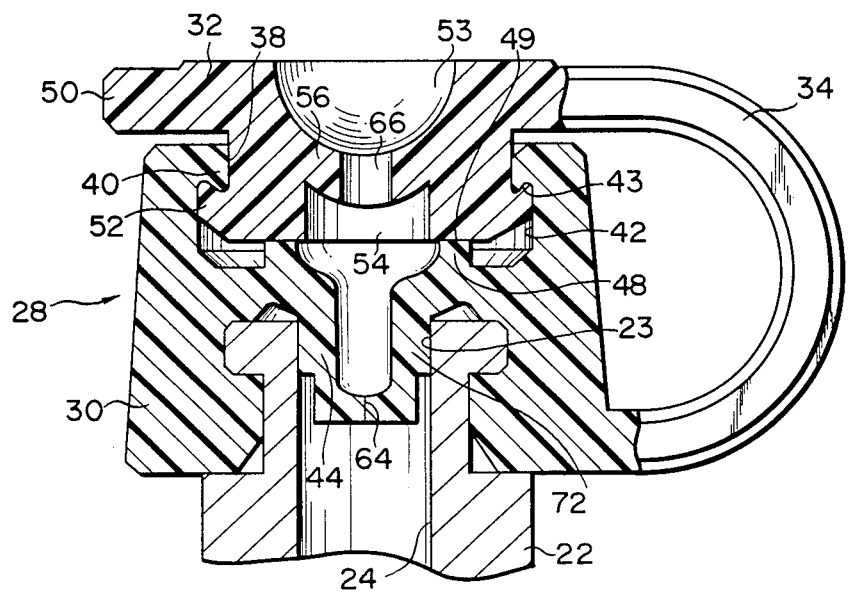
Figure 12:
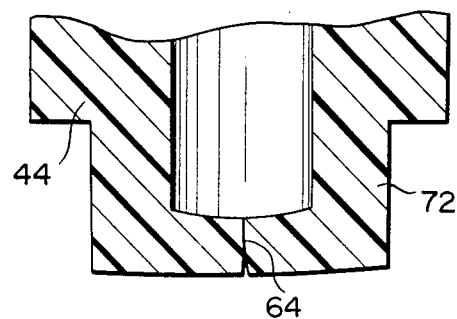

Description may now be made with reference to FIGS. 11 and 12 of a forceps stopcock according to a fourth embodiment of this invention. An insertion hole 66 as an insertion section is formed in the thin-walled section 56 of the cap 32. The valve section 44 of the cylindrical body 30 includes a blind stepped cylindrical body 72. This cylindrical body 72 is inserted into the insertion channel 24 through the insertion port 23. The larger diameter section of the cylindrical body 72 has a larger diameter than that of the insertion channel 24, and is fitted into the insertion channel. The bottom of the cylindrical body 72 is provided with a slit 64 allowing for the insertion of forceps.

With the fourth embodiment, the cylindrical body 72 is fitted into the insertion channel 24 and pressed radially inward by the inner wall of the insertion channel 24. As shown in FIG. 12, the upper portion of the slit 64 is pressed inward to close air-tightly. Even when, therefore, the internal pressure in the insertion channel 24 rises to push the valve section 44 upward, the slit 64 is not opened, thereby reliably preventing the leakage of air or filth from the patient's coeliac cavity. The cylindrical body 72 acts as clamping means for clamping the valve section 44.

Figure 13:
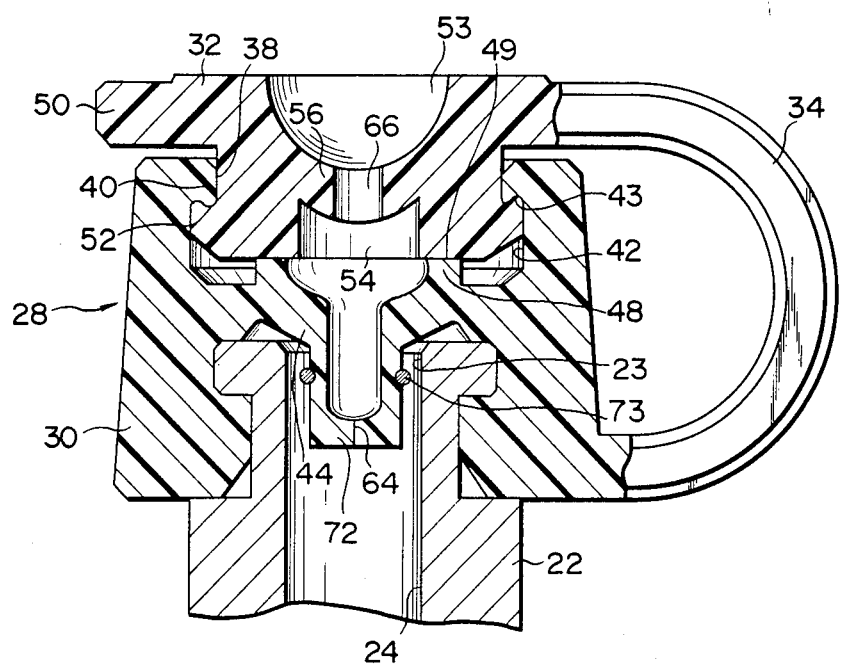
FIG. 13 is a sectional view of a forceps stopcock according to a fifth embodiment of the invention.

FIG. 13 shows a forceps stopcock according to a fifth embodiment of this invention. With this embodiment, the cylindrical body 72 of the valve section 44 has a smaller diameter than that of the insertion channel 24. A metal ring 73 as clamping means is fitted on the outer periphery of the cylindrical body 72 to close the slit 64 in an air-tight fashion. With this embodiment, the same effect as the fourth embodiment can be obtained.

Description may now be made with reference to FIG. 14 of a forceps stopcock according to a sixth embodiment of this invention. With this embodiment, a hollow region 78 is provided at the center of the cap 32. The hollow region 78 defines the first and second thin-walled sections 56, 74. These thin-walled sections 56, 74 face each other at a prescribed interval in the axial direction of the cap 32. Under the condition in which the cap 32 is engaged with the cylindrical body 30, the first thin-walled section 56 facing the cylindrical body 30 is provided with a slit 58 to allow for the insertion of the forceps 26, and the second thin-walled section 74 is provided with an insertion hole 76. This insertion hole 76 has a smaller diameter than the forceps 26 to be inserted.

With the sixth embodiment of FIG. 14, the forceps sealing member, that is, the first and second thin-walled sections 56, 74 seal the forceps at a larger number of spots, thereby ensuring the more hermetic sealing of the forceps stopcock 28 when the forceps 26 is inserted into the insertion channel 24 through the forceps stopcock 28, and consequently more reliably preventing the leakage through the endoscope channel of the air or filth drawn from the patient's coeliac cavity.

The parts of the second to sixth embodiments which are the same as those of the first embodiment are denoted by the same numerals, the detailed description thereof being omitted.

What is claimed is:

1. An endoscope forceps stopcock fitted to an insertion mouthpiece provided at an insertion port of an insertion channel of an endoscope allowing for the insertion of medical instruments which comprises:
   a substantially cylindrical first member fitted to the insertion mouthpiece, said first member including an engagement section formed at one end opening thereof to be detachably engaged with the insertion mouthpiece, another engagement section formed at another end opening of the first member, and a valve section provided between both engagement sections in the first member to close the insertion port of the insertion channel;
   a second member removably fitted to the another engagement section of the first member and having a second valve section located to face the first valve section, said first and second valve sections having insertion sections allowing for the insertion of medical instruments, respectively, and at least one of the insertion sections being normally closed by the elasticity of the valve section; and
   a coupling member for connecting the first and second members.

2. An endoscope forceps stopcock according to claim 1, wherein said first and second valve sections are arranged to define a space between them.

3. An endoscope forceps stopcock according to claim 1, wherein said first and second members and coupling member are integrally prepared from an elastic material.

4. An endoscope forceps stopcock according to claim 1, wherein said insertion section of the first valve section is provided with an insertion hole having a diameter smaller than that of the medical operation instruments, the insertion hole being positioned substantially concentric with the insertion channel.

5. An endoscope forceps stopcock according to claim 4, wherein said insertion section of the second valve section is provided with a slit longer than the diameter of the medical operation instruments.

6. An endoscope forceps stopcock according to claim 1, wherein said insertion section of the first valve section is provided with a slit longer than the diameter of the medical operation instruments.

7. An endoscope forceps stopcock according to claim 6, wherein said insertion section of the ssecond valve section is provided with an insertion hole narrower than the diameter of the medical operation instruments; and said slit and insertion hole are set substantially concentric with the insertion channel.

8. An endoscope forceps stopcock according to claim 6, wherein said slit extends in the axial direction of the insertion channel, and is made progressively narrower from the second member to the insertion channel.

9. An endoscope forceps stopcock according to claim 6, wherein said first valve section is provided with tightening means for pressing the slit to close it.

10. An endoscope forceps stopcock according to claim 9, wherein said first valve section is provided with a bottomed cylinder extending into the insertion channel; said slit is formed in the bottom of the cylinder; said cylinder is engaged with the insertion channel, and is provided with a larger diameter section whose outer diameter is made larger than the diameter of that of the insertion channel which is pressed radially inward by the inner wall of the insertion channel, said larger diameter section constituting said tightening means.

11. An endoscope forceps stopcock according to claim 1, wherein said second member includes an engagement section formed on the end of the second member away from the first member with the second valve section interposed therebetween and being capable of detachably engaging with the insertion mouthpiece.

12. An endoscope forceps stopcock according to claim 1, wherein said second member includes a third valve section facing the second valve section at a prescribed interval, and an insertion section formed in the third valve section allowing for the insertion of the medical operation instruments.

* * * * *